United States Patent [19]

Lichtenberger

[11] Patent Number: 4,918,063
[45] Date of Patent: Apr. 17, 1990

[54] METHODS AND COMPOSITIONS EMPLOYING UNIQUE MIXTURES OF POLAR AND NEUTRAL LIPIDS FOR PROTECTING THE GASTROINTESTINAL TRACT

[75] Inventor: Lenard M. Lichtenberger, Houston, Tex.

[73] Assignee: Board of Regents, The University of Texas System, Austin, Tex.

[21] Appl. No.: 15,394

[22] Filed: Feb. 17, 1987

[51] Int. Cl.$^4$ .............................................. A01K 31/685
[52] U.S. Cl. ..................................... 514/78; 514/547; 514/925
[58] Field of Search .......................... 514/78, 547, 925

[56] References Cited

FOREIGN PATENT DOCUMENTS 0074251 of 0000 European Pat. Off. .
0092121 of 0000 European Pat. Off. .
0110498 of 0000 European Pat. Off. .
0213724 of 0000 European Pat. Off. .
2556592 of 0000 Fed. Rep. of Germany .
2445146 of 0000 France .
2080324 of 0000 United Kingdom .

OTHER PUBLICATIONS

Chemical Abstracts 106:48070g, 1987.
Ikegami, et al., (1980), Chem. Ab., 92(3):62, Abstract No. 15567.

Primary Examiner—Leonard Schenkman
Attorney, Agent, or Firm—Arnold, White & Durkee

[57] ABSTRACT

Disclosed are compositions composed of unique mixtures of phospholipids and neutral lipids and methods of employing such compositions to treat the luminal lining of the gastrointestinal tract in the prevention or treatment of ulcerogenic processes such as peptic ulcer disease and inflammatory bowel disease. Compositions including mixtures of saturated or unsaturated phospholipids, together with saturated or unsaturated triglycerides and/or sterols, are shown to provide a surprising ulcer protective efficacy in experimental models. Further enhancement of activity is found upon the addition of a polyvalent cation or antioxidant to the various lipid mixtures.

15 Claims, 5 Drawing Sheets

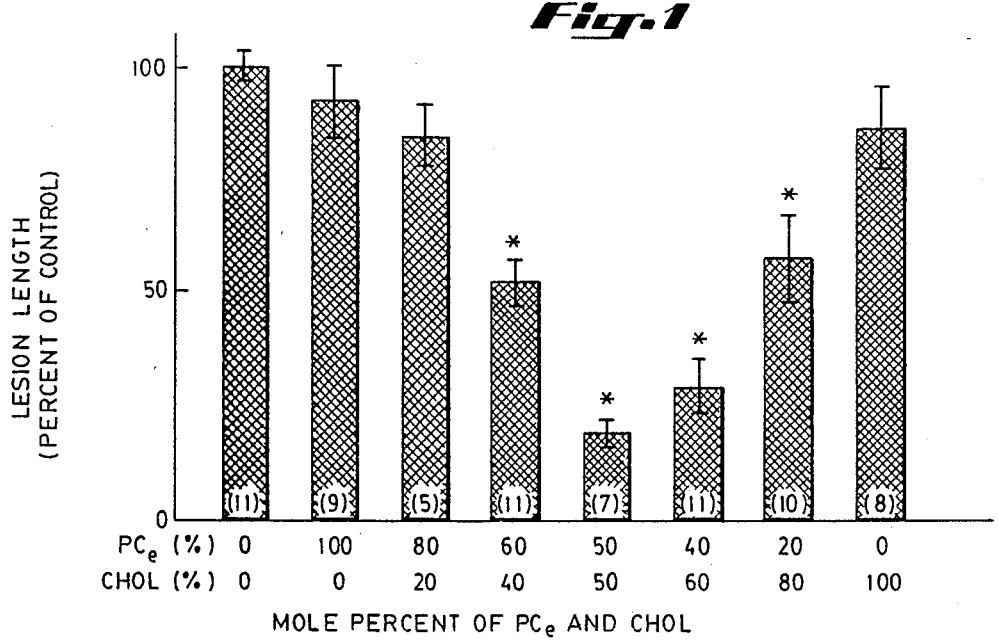
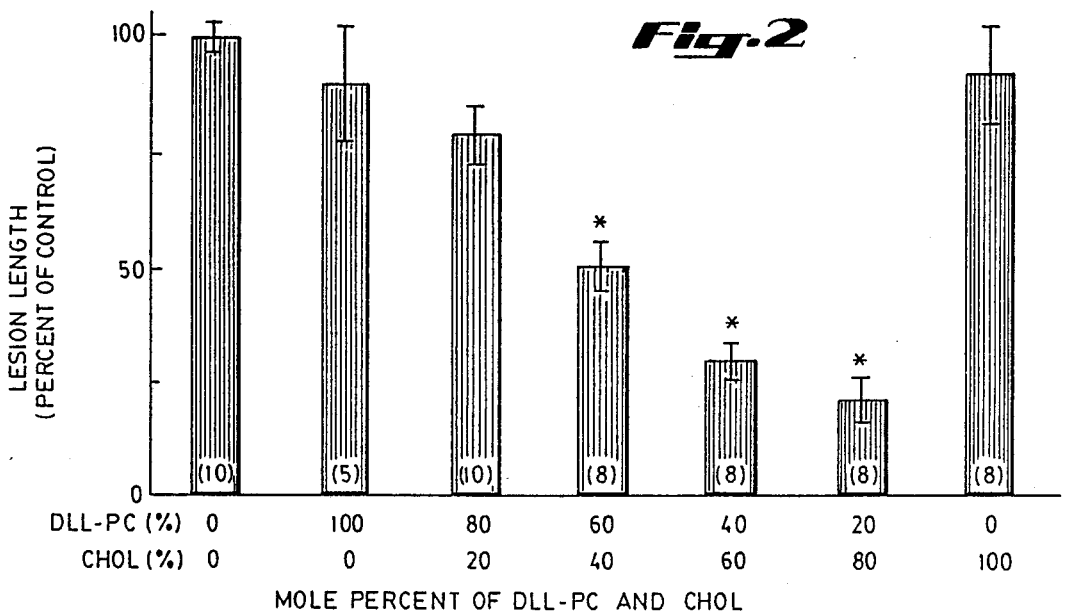

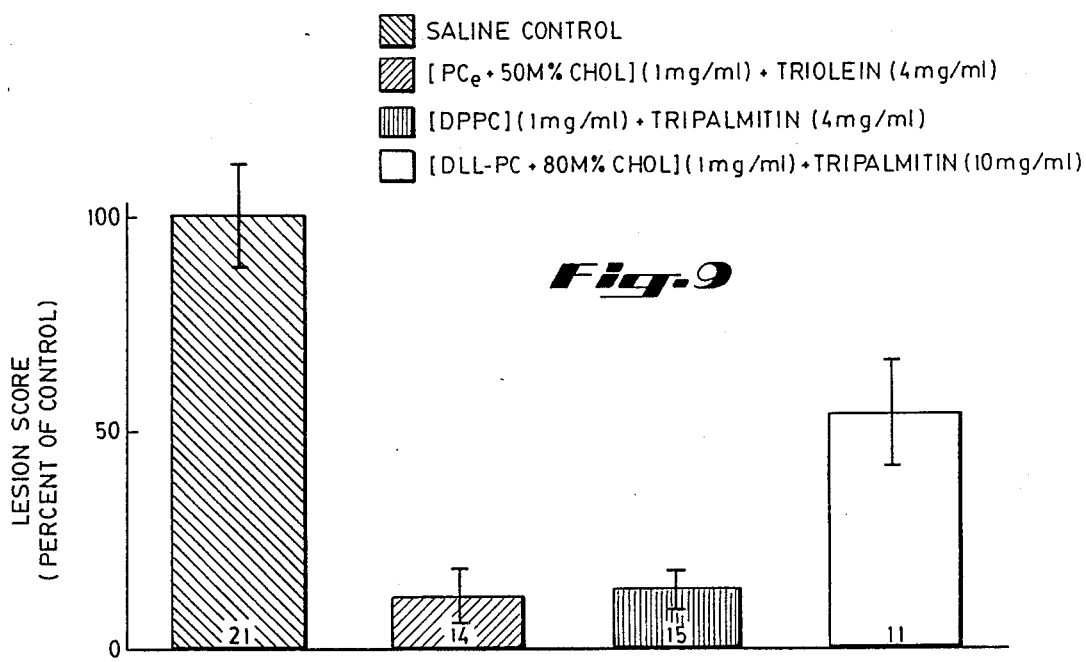
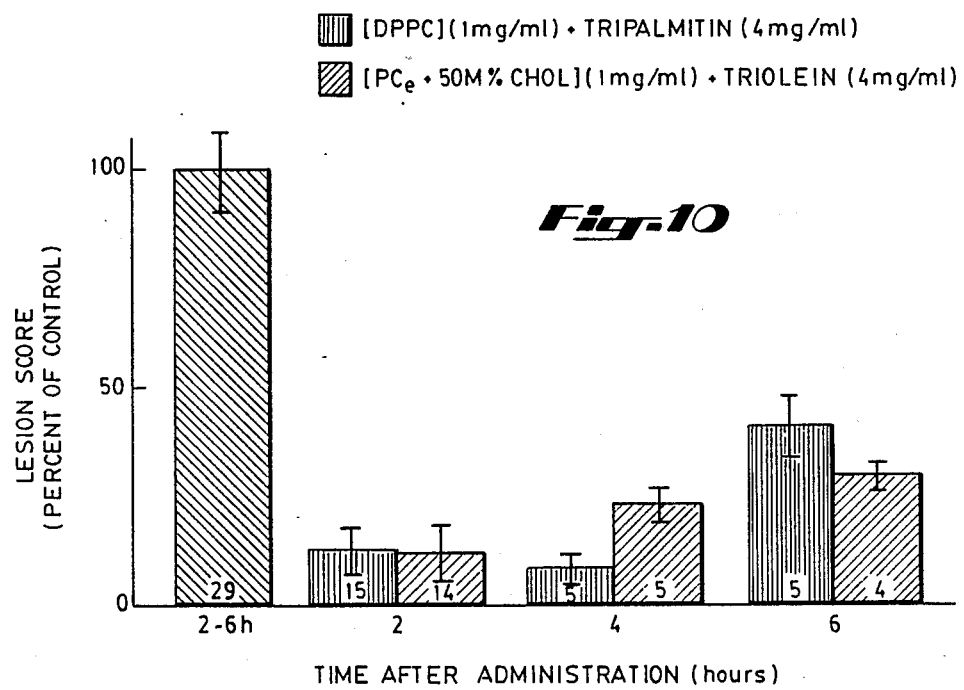

METHODS AND COMPOSITIONS EMPLOYING UNIQUE MIXTURES OF POLAR AND NEUTRAL LIPIDS FOR PROTECTING THE GASTROINTESTINAL TRACT

BACKGROUND OF THE INVENTION

The government may own certain rights in the present invention pursuant to NIH grant AM 33239.

FIELD OF THE INVENTION

The present invention relates to pharmaceutical compositions and methods for protecting the luminal lining of the gastrointestinal tract from ulceration. In particular, the present invention relates to compositions which include unique mixtures of phospholipids, triglycerides and/or cholesterol which are useful for the treatment or prevention of ulceration of the lining of the gastrointestinal tract.

DESCRIPTION OF THE RELATED ART

Gastrointestinal ulcer disease, in particular, peptic ulcers, affect 5-15% of the United States population. Moreover, this disease is not restricted to the more industrialized Western culture--indeed, gastric ulceration is even a more serious problem in the Orient. One ulcer disease, particularly worrisome to pediatricians, occurs in the premature infants. This condition, known as necrotizing enterocolitis, affects 10-15% of newborns having a birth weight of under 1.5 kg and results in severe ulceration of the small intestine, which frequently requires surgery. The etiology of this condition, like that of peptic ulcer disease, is not understood but it has been postulated that the primary defect lies in an abnormal mucosal defense mechanism against luminal damaging agents.

Severe ulceration of the gastrointestinal mucosa can also spontaneously occur in the lower bowel (distal ileum and colon) in a spectrum of clinical disorders called inflammatory bowel disease (IFBD). The two major diseases in this classification are Ulcerative Colitis and Crohn's Disease which are associated with severe mucosal ulceration (frequently penetrating the wall of the bowel and forming strictures and fistulas), severe mucosal and submucosal inflammation and edema, and fibrosis. Clinically, patients with fulminant IFBM can be severely ill with massive diarrhea, blood loss, dehydration, weight loss and fever. The prognosis of the disease in not good and frequently requires resection of the diseased tissue. The etiology of IFBD is also poorly understood.

There are many drugs currently on the market to treat peptic ulcer disease. Most of these drugs are directed to neutralizing or inhibiting gastric acid secretion. Notable of the antiulcer compositions are anticholinergics and antihistamines both of which can result in a multitude of undesirable side effects in addition to blocking gastric acid secretion. This form of therapy is based on the tenet "no acid, no ulcer". Although it appears that peptic ulcers will not form in the complete absence of gastric acid, it is generally recognized that not all ulcer patients exhibit enhanced gastric acid output. In fact, gastric ulcer patients as a group have abnormally low gastric acidity. Thus, it has been suggested that gastric acidity may only be an aggravating factor and not a primary cause of gastrointestinal ulcerogenesis.

There is little consensus on the proper medical treatment of necrotizing enterocolitis. Frequently afflicted infants are managed by intravenous hyperalimentation and surgery when life-threatening strictures or perforations result. The medical treatment of inflammatory bowel disease in general is directed to controlling rather than curing the disease. Typical protocols employ steroids and the sulfa drug, Azulfidine (Salicylazosulfapyridine). Although these drugs reduce the mucosal inflammation, diarrhea and even blood loss in chronic inflammatory processes, they have little efficacy in treating the more fulminant forms of the disease. Furthermore, they cause a host of side effects of varying severity in the patients.

An alternative explanation of ulcer incipiency involves the belief that G.I. ulceration develops in individuals that have a defect in a putative "gastrointestinal mucosal barrier." This defect permits luminal damaging agents (acid, enzymes, bile salts, bacteria) to penetrate the surface lining and thereafter promote ulcerogenesis.

It is presently unclear how the normal gastrointestinal (GI) epithelium protects itself from these insults. Indeed, the answer to this fundamental question has long been sought, since it certainly remains a paradox why the stomach does not digest itself while it is constantly bathed in an extremely acidic and proteolytic environment. Conversely, the clinically important question remains as to how and why the element of protection is removed or circumvented in peptic ulcer disease, necrotizing enterocolitis and inflammatory bowel disease. A great deal of research has been performed to answer these important questions. Investigators have postulated that the mucosa is protected by a putative "gastrointestinal mucosal barrier" which prevents the back diffusion of hydrochloric acid and other potentially toxic agents from the lumen into the epithelium. Disruption of this mucosal barrier, results in the development of GI erosions. Although a wide variety of damaging agents such as aspirin, bile salts, hydrochloric acid and alcohol certainly will cause G.I. ulceration if present in high enough concentrations, it is generally believed that the primary cause of ulcer disease in a majority of patients is attributable to a natural defect in the "G.I. mucosal barrier."

Unfortunately, as noted above, most of the existing pharmacological approaches to the treatment of gastrointestinal disease are directed to treating either the gastric acid secretions, for example, through the use of anticholinergics, antihistaminics, and/or antacids, reducing mucosal and submucosal inflammation (steroids) or by physically treating the ulcer itself, for example, with a coating agent such as sucralfate. While the treatment of gastric acid secretion has served to provide some degree of symptomatic and pain relief and occasionally promote ulcer healing, their use is often complicated by undesirable side effects and/or promotion of an acid rebound effect. Sucralfate, on the other hand, is directed to treating the ulcerated tissue directly by forming a physical barrier to gastric contents, and thus does not serve an ulcer preventative function. Moreover, peptic ulcers readily recur at a high rate once patients are withdrawn from therapy with $H_2$ antagonists or sulcrafate. Similarly the underlying defect in the mucosal barrier which increases a patients susceptability to inflammatory bowel disease has yet to be identified and it is clear that our present forms of medical therapy for this condition merely treat the symptoms instead of the origin of the disease.

It has been observed by the present inventor that the mucosal surface of certain regions of the gastrointestinal tract have remarkable hydrophobic characteristic that make it non-wettable (i.e.—water-repellant) to the luminal contents. It was of interest that the most hydrophobic gastrointestinal tissues (e.g., the stomach, esophagus and colon) are those regions most susceptible to mucosal ulceration or inflammation. Furthermore, it has been observed that experimental chemicals which induce gastric ulcerogenesis or colitis in laboratory animals result in a marked attenuation of the non-wettable property of the affected mucosal region.

Accordingly, the present invention derives in part from such observations by recognizing a need for a treatment method which is directed to restoring or maintaining the normal hydrophobic character of the luminal lining and thereby prevent or retard the deleterious effects of cytotoxic chemicals in the lumen (e.g., $H^+$, proteolytic enzymes, edotoxin) to the mucosal lining. Moreover, there is a need for essentially nontoxic agents which may be administered in a convenient dosage form, for example, in a liquid or suspension form, that is well tailored to treat the luminal lining quickly and effectively.

SUMMARY OF THE INVENTION

In its most general and overall scope, the present invention is directed to the realization that by treating the luminal surface of the gastrointestinal tract with an agent having the ability to increase or maintain its hydrophobic character, the luminal lining may thereby be protected from the deleterious effects of aqueous cytotoxic chemicals in lumen, for example, gastric acid and digestive enzyme secretions. The invention is directed in particular to unique mixtures of zwitterionic phospholipids together with neutral lipids, for example, sterols and/or triglycerides, which can provide the luminal lining with a very consistent and long-lasting protection from chemical and idiopathic gastrointestinal ulcerogenesis. Thus, the term phospholipids, as referred to herein, relates generally to phospholipids which have a positively charged nitrogen at the site of application. For example, the amine may be either a quaternary amine or an amine that is ionized at the pH of the stomach.

Pharmaceutical compositions of the present invention, in one embodiment, include a saturated phospholipid having aliphatic substitutions ranging from 8 to 32 carbon atoms, together with a saturated triglyceride, having saturated aliphatic substitutions ranging from 4 to 32 carbon atoms, the phospholipid and triglyceride being disposed in a pharmaceutically acceptable diluent.

As used herein, a saturated phospholipid is defined as a phospholipid containing only saturated aliphatic substitutions of from 8 to 32 carbon atoms, and saturated triglyceride is defined as a triglyceride having saturated aliphatic substitution of from 4 to 32 carbon atoms.

Although virtually any combination of a saturated phospholipid and saturated triglyceride will provide the benefits of the present invention, in a preferred embodiment the saturated phospholipid is dipalmitoyl-phosphatidylcholine (DPPC), dimyristoyl phosphatidylcholine, distearoyl phosphatidylcholine, and the saturated triglyceride is tripalmitin (TP), trimyristin, and/or tristearin.

Although it has previously been found that saturated phospholipids have some degree of antiulcer activity in and of themselves, the present invention embodies the discovery that the addition of a triglyceride (preferably saturated) to the saturated phospholipid-containing composition will enhance the antiulcer effect of the saturated phospholipid to a surprising extent. For example, when the saturated phospholipid dipalmitoyl phosphatidylcholine (DPPC) is intragastrically administered to rats at a low threshold concentration of 1 mg/ml, 2 hrs prior to being challenged with strong acid, a marginal 5-10% reduction in lesion score is recorded. In contrast, addition of the saturated triglyceride tripalmitin (TP) to the DPPC suspension induced a dramatic dose-dependent increase in protection against acid-incuded gastric ulcerogenesis with <90% reduction in lesion score being recorded when TP was added at concentrations of 4 mg/ml or greater. Furthermore, the protection provided by this mixture was observed to be long-lasting, with lesion score reduced by 75% when the lipids were administered 6 hrs prior to the acid challenge.

Interestingly, compositions which include only a saturated phospholipid together with an unsaturated triglyceride have a lessened antiulcer activity in the experimental systems employed by the present inventor. Moreover, saturated phospholipid-containing compositions are found to lose their activity upon the addition of stoichiometric amounts of cholesterol, or other sterols, to the mixture. Although it is unclear why this is the case, it is hypothesized that the addition of cholesterol, or other sterols, to saturated phospholipid-containing compositions apparently serves to disrupt the association of phospholipid structures and thereby prevents their interaction with the luminal lining to form a uniform hydrophobic lining.

In one embodiment of the invention, the saturated phospholipid and saturated triglyceride are included in weight ratios ranging from 1:1 to 1:10, and more preferably in weight ratios ranging from 1:2 to 1:15. In fact, a weight ratio of 1:4 has been found to provide the most superior antiulcer activity of all of the presently disclosed antiulcer compositions.

In further embodiments, pharmaceutical compositions are provided which comprise an ulcer protective amount of the combination of an unsaturated phospholipid, defined as a phospholipid having at least one unsaturated aliphatic substitutions ranging from 8 to 32 carbon atoms, together with a sterol having an aliphatic substitution of from 1 to 10 carbon atoms at the number 17 carbon, both together in a pharmaceutically acceptable diluent.

Although cholesterol is the preferred sterol, other sterols such as desmosterol, B-sitosterol or estradiol will function equally well. However, in that it is generally desirable to keep the potential toxicity of the present compositions at a minimum, it is suggested that only nonbiologically-active sterols be included. Therefore, for example, one would not typically desire to include a sterol having hormonal activity such as an estrogen, androgen, corticosteroid, progestigen, or anabolic steroid. Therefore, due to its ready availability, low cost and lack of potential toxicity, cholesterol is desirably employed in the formulation of unsaturated phospholipid-containing compositions.

In a preferred embodiment, the unsaturated phospholipid and sterol-containing compositions are formulated to include the unsaturated phospholipid and sterol in mole percent ratios ranging from about 4 to about 0.25, or more preferably, in mole percent ratios ranging from about 1.5 to about 0.25, respectively.

In certain preferred embodiments, the unsaturated phospholipid and sterol-containing compositions are formulated to include egg phosphatidylcholine, or the poly-unsaturated dilinoleoyl-phosphatidylcholine. However, virtually any lipid as defined herein will provide benefits in accordance with the inventor.

It has further been determined that the antiulcer activity of unsaturated phospholipid and sterol-containing compositions is greatly improved upon the addition of a triglyceride to the formulation. The triglyceride in such compositions may be either saturated or unsaturated. However, it has been found that there is some degree of preference in terms of which saturated or unsaturated triglyceride is employed with which unsaturated phospholipid. For example, it is preferred to employ dilinoleoyl phosphatidycholine (DLL-PC) with the saturated triglyceride tripalmitin. However, where the selected unsaturated phospholipid is egg phosphatidylcholine, the preferred triglyceride is the unsaturated triglyceride triolein.

It should be noted that the protective activity of the lipid mixtures of the present invention does not depend upon the ester bonding between the fatty acid side chain and the constituent phospholipid and/or triglyceride. Full activity is retained when the ester bonding is substituted with an ether bonded fatty acid said chain.

The phospholipid compositions, whether based on saturated or unsaturated phospholipids, are typically formulated into colloidal or liposomal suspensions using an aqueous medium or diluent to provide a composition having a concentration ranging from about 0.5 to about 10 mg/ml of suspension, depending upon the intended application and ulcer-protective strength of the combination employed. For example, for the treatment of peptic ulcer disease by oral administration to the stomach, a dose range of from 1 to about 4 mg/ml is generally preferred. However, for application to the lower bowel, higher concentrations may be indicated, particularly for more severe luminal erosions such as in ulcerative colitis.

Although the particular aqueous diluent is not particularly crucial, Applicant has found that isotonic saline provides a consistently stable and efficacious formulation. However, it is believed that lipid deposition and adsorption to the mucosal surface may be accelerated by the presence of polyvalent cations in the diluent solution.

In formulating the phospholipid mixtures, the desired amount of the selected lipids are simply placed into a suitable container and an appropriate amount of isotonic saline, or other aqueous medium, added. The entire mixture is then vortexed, sonicated or otherwise vigorously admixed for several minutes to suspend the lipids. In some cases the temperature may be raised above the transition temperature for a phospholipid to promote the formation of a colloidal suspension. It has been found that sonication is preferred for unsaturated phospholipid/triglyceride compositions as well as for other lipid compositions which include a saturated triglyceride. For other unsaturated phospholipid-containing compositions, vortexing is generally preferred.

Compositions formulated in this manner are generally stable for at least one week, and typically longer, either at 4° C. or room temperature. However, some degree of settling of the lipids may occurs upon storage of the composition for extended periods. Upon settling, the compositions may be readily regenerated by simply shaking or vortexing it to resuspend the lipids. There is generally no requirement that lipid aggregates be dispersed in that generally such aggregates have been found to exhibit the same or greater activity as totally dispersed suspensions.

In general, it has been determined that the addition of a polyvalent cation, for example, a heavy metal ion, to the formulation of any of the foregoing compositions will improve their antiulcer activity. It is hypothesized that the polyvalent ions interact with the negatively charged region of the phospholipid in a manner to facilitate its adsorption to the luminal lining and thereby increase its efficacy in maintaining luminal hydrophobicity. It is postulated that virtually any polyvalent cation, and in particular, heavy metal ion, will function in this regard, and should typically be included in a molar ratio of between about 0.5 and 20 moles of phospholipid to moles of metal ion. Due to their potential toxicity, certain heavy metals should not be employed, for example, mercury, which has a very high nephrotoxicity. However, metal ions such as copper, zinc, gold or aluminum are generally well tolerated at effective concentrations, and thus may be included to improve the efficacy of the phospholipid compositions. The heavy metals are typically added in the form of metal ions present in the aqueous medium used to suspend the lipid mixtures.

The invention further embodies the realization that the addition of both lipid and water soluble vitamins (vitamins A, E and C) and other chemical anti-oxidants with the capability of scavenging free radicals can further enhance and prolong the anti-ulcer efficacy of these lipid mixtures. This is likely attributable to their ability to prevent the oxidative destruction of unsaturated phospholipids.

Accordingly, the present invention is directed in its most general scope to a method of protecting the luminal lining of the gastrointestinal tract of a subject against ulceration, the method including administering an effective amount of one of the foregoing compositions to the lining. Protection against ulceration is thus provided to the luminal lining by administering to it an amount of one of the foregoing compositions that is effective to maintain the hydrophobicity thereof.

The compositions of the present invention may be employed together with a non-steroidal antipyretic or anti-inflammatory agent, such as aspirin or the like, as a means of preventing or reducing other ulcerogenic side effects. The non-steroidal agents may be formulated into the compositions by including them into the aqueous diluent, by adding them to the compositions post-formulation, or by simply co-administering them together with the anti-ulcer composition. Where the lipids employed tend to form liposomes, for example, in the case of unsaturated phospholipid/cholesterol compositions, it may be particularly desirable to include the non-steroidal agent into the mixture prior to vortexing or sonication in that this will allow at least a proportion of the agent to be liposomally encapsulated, thereby improving the protective action of the lipid mixture. However, an adequate protective effect can be obtained by simple co-administration. Thus, such compositions, however formulated, will function to prevent the ulcerogenic action of such ulcerogenic agents and, in this embodiment, function to simultaneously provide the subject receiving such an agent with a suitable relief from pain, fever, bleeding, diarrhea and/or inflammation.

BRIEF DESCRIPTION OF THE DRAWINGS

FIG. 1. A graphical illustration of the ulcer protective activity upon acid challenge of the combination of Egg phosphatidylcholine ($PC_e$) together with varying mole % amounts of cholesterol. The asteriks represent cholesterol embodiments showing the most clinically significant activity. Although neither $PC_e$ nor Chol protected against acid-induced gastric lesions on their own, unique mixtures of the polar and non-polar lipids have a clear protective action with a maximal 85% reduction in lesion score being produced by a mixture of $PC_e$+50M % Chol. In this, and the subsequent experiments disclosed in the following figures (unless indicated otherwise), animals were intragastrically treated with 1 ml of the lipid test solution (total lipid conc=3 mg/ml), 2 hrs before being intragastrically challenged with 1 ml of 1N HCl. The rats were sacrificed 1 hr later at which time lesion score was analyzed under coded conditions.

FIG. 2. A graphical illustration of the ulcer protective activity, upon acid challenge, of the combination of dilinoleoyl phosphatidyl choline (DLL-PC) together with varying mole % amounts of cholesterol As with FIG. 1, the asteriks are representative of preferred mole % rations. As with the FIG. 1 experiments, although neither DLL-PC nor Chol protected rats against acid-induced gastric lesions on their own, unique mixtures of the two lipids produced profound protection with a maximal (85% protection) effect being observed with a mixture of DLL-PC+80M % Chol.

FIG. 9. Protective effect of mixtures of polar and non-polar lipids against ethanol-induced gastric lesions. This figure demonstrates that mixtures of phospholipids/Chol/TG had profound protective action against another gastric ulcerogenic challenge, intraluminal administration of 1 ml of 100% ethanol. As before, lipid mixtures were administered 2 hrs before challenge and the rats sacrificed 1 hr after challenge.

FIG. 10. Time-dependance of protective effect of mixtures of polar and non-polar lipids against ethanol-induced gastric lesions. This figure demonstrates that similar to the protective against acid-induced damage, the protective action of two mixtures against ethanol-induced gastric injury was long acting and still provided significant protection 6 hrs after administration.

DETAILED DESCRIPTION OF THE PREFERRED EMBODIMENTS

I. Introduction

Figure 3:
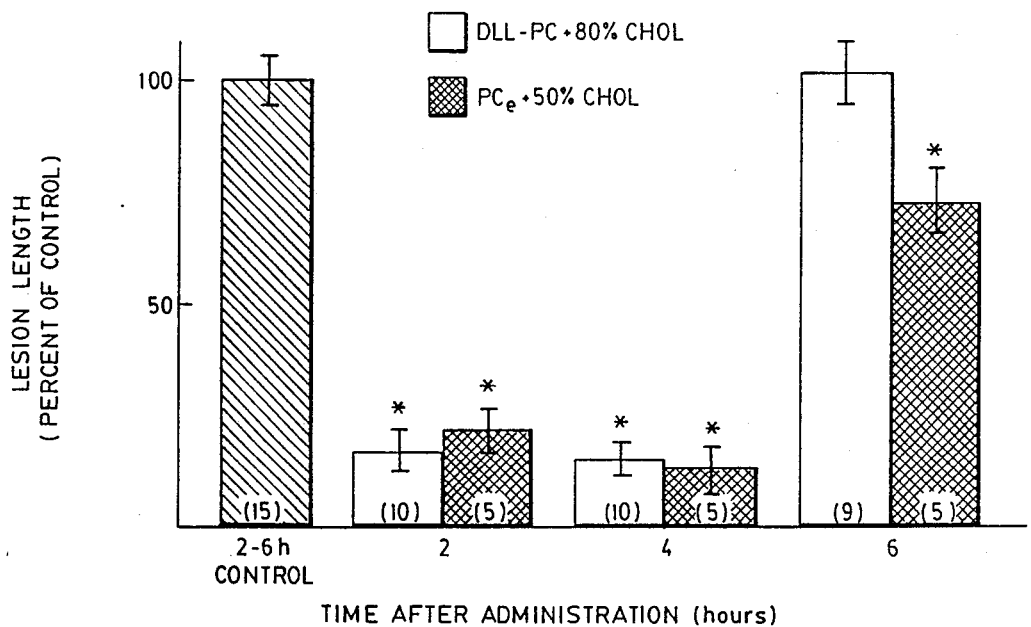
FIG. 3. Time-dependance of the protective effect of mixtures of unsaturated phospholipids (Egg-phosphatidylcholine, $PC_e$; and dilinoleoylphosphatidylcholine, DLL-PC) together with cholesterol (50 and 80M %) against acid-induced gastric lesions. This graph illustrates the protective action of the mixtures of unsaturated phospholipid and cholesterol against acid-induced lesions was long-lasting and dissipated between 4-6 hrs post-injection. In this experiment the lipid mixture was intragastrically administered 2, 4 and 6 hrs prior to the acid-challenge. As before, the rats were sacrificed 1 hr after acid-challenge.

Recent studies by the present Applicant have indicated that many of the phospholipids found in a pulmonary fluid are also found along the length of the gastrointestinal tract, from the esophagus to the colon. These phospholipids appear to be concentrated on the mucosal surface which separates the digestive and absorptive epithelium from the luminal contents. The functional importance of phospholipids has been studied in greatest detail in the lung. It is now well recognized that pulmonary surfactants, which are high in phospholipids, play a vital role in minimizing the surface forces at the level of the alveoli, allowing the alveoli to remain open throughout the respiratory cycle.

There is a certain amount of evidence that the surface properties of surfactants also play a role in reducing the movements of extracellular fluids from the blood into the extracellular space. Perhaps related to this property, Applicant has recently found that surfactants, not unlike commercially available water repellants used to treat material surfaces, will make biological tissues non-wettable. This action provides the tissue with a hydrophobic lining that will resist the penetration of water molecules across its surface.

In early experiments it was found that certain natural and synthetic phospholipids could both maintain the hydrophobic character of the luminal lining and retard the untoward effects of ulcerogenic compounds to a certain degree (see, for example, Lichtenberger et al. (1983), Science, 219:1327; Butler et al. (1983) Am. J.

*Physiol.*, 244:G645; Hills et al. (1983), *Am. J. Physiol.*, 244:G562; and Dial et al. (1984), *Gastroenterology*, 87:379). However, the protective efficacy of these phospholipid suspensions varied widely between experiments, and when present was quite transient.

Upon further experimentation it has been found that mixtures of phospholipids together with neutral lipids, for example, sterols and/or triglycerides, can provide the luminal lining with long-lasting and very consistent protection from chemical and idiopathic gastrointestinal ulcerogenesis. For example, experimental findings, disclosed in detail below, demonstrate that mixtures of unsaturated phospholipids and cholesterol in various proportions can provide a marked protection from acid-induced ulcerogenesis. This protection is found to be surprisingly superior to the protection provided by phospholipids alone which have either little or no protective action on their own. Moreover, this protective effect is even further enhanced upon the addition of a triglyceride, either saturated or unsaturated, to the mixture. Compositions formulated to include a saturated phospholipid together with a saturated triglyceride are found to provide the most effective protection.

Curiously, though, much smaller enhancement in protective activity is obtained with compositions formulated to include a saturated phospholipid together with an unsaturated triglyceride. Moreover, the activity of saturated phospholipids standing alone is totally abolished by the addition of a sterol in stoichiometric amounts to the mixture. In contrast, unsaturated phospholipids, standing alone, appear to provide little or no protective effect and require the addition of a sterol such as cholesterol. The reason for this molecular specificity between polar and non-polar lipids is not known but may, in part, be attributable to the fact that saturated phospholipids and saturated triglycerides pack tightly with one another forming a compact and stable hydrophobic layer. Furthermore this level of organization is disrupted by the addition of cholesterol or unsaturated triglycerides to the mixture. In contrast by virtue of their non-linear fatty acid side chains unsaturated phospholipids do not pack tightly with one another and the addition of cholesterol and triglycerides to the mixture promote molecular contraction and stability of the hydrophobic layer.

The lipids which are the subject of this invention are naturally occurring substances extractable from plant and animal sources or can be synthesized by various known processes. Furthermore, most of the lipids are commercially available, as they are starting materials for a wide class of soaps, pharmaceutical preparations, and biochemical research materials.

For oral administration, the compounds can be administered in substantially pure, undiluted form; as a supplement to infant formula or in various pharmaceutical dosage forms such as capsules, liposome carriers, aerosol sprays, dispersions, aqueous suspensions, solutions, or the like. In that oral administration is typically the indicated route for treatment of gastric ulcer disease, a preferred composition for such application is a colloidal or liposomal suspension of the phospholipid and associated neutral lipid. Moreover, suspensions may be indicated for other routes as well, such as administration to the lower bowel by means of an enema, or for direct infusion to the bowel.

While wishing not to be limited to the following theory, Applicant's invention is based on the principle that the zwitterionic phospholipids which carry a positive terminal charge, will be attracted to the negatively charged surface membrane of the G.I. tract. These molecules will in turn orient in such a way so that their long hydrocarbon chains are extending outwards into the lumen. This results in the formation of a uniform hydrophobic layer over the tissue, which cannot be penetrated by hydrophilic damaging agents. This prevents water soluble damaging agents (e.g., acid, microbial toxins, proteolytic enzymes) from coming in contact with the tissue, and protects the tissue from injury. When the hydrocarbon side chains are not straight, for example, due to the presence of cis unsaturated bonds, cholesterol is believed to be required to promote molecular packing. In turn, the cholesterol molecule is believed to enhance the hydrophobicity of the hydrocarbon layer. The thickness and stability of this layer may be increased substantially by the addition of triglycerides to the mixture, which may coat the luminal aspects of the adsorbed phospholipid (and cholesterol) layer by undergoing hydrophobic bonding with the extending fatty acid side-chains.

As indicated above it is believed that the addition of neutral lipids, in the form of glycerides or sterols, to the phospholipid compositions appear to stabilize this interaction with the luminal lining. This stabilization effect is most readily demonstrated by, for example, both the increase in duration of activity, and in the increase on both efficacy and potency of the antiulcer protection of the neutral lipid containing compositions over compositions which include only phospholipids. Again, the mechanism is unclear. Another possible explanation may lie in the finding that the addition of neutral lipids to the suspension of charged lipids (i.e.—zwitterionic phospholipids) appears to accelerate the deposition of precipitation of the lipid complex from the suspension. Thus, phospholipid suspensions containing neutral lipids may coat biological surfaces at a faster rate and to a greater extent than the phospholipids standing alone.

In the practice of this invention, Applicant has found that gastric mucosa pretreated with either synthetic or natural phospholipids becomes virtually impermeable to acid. This property was most dramatically demonstrated in vivo, where it was observed that rats pretreated with phospholipid resisted severe gastric mucosal damage after direct challenge to a strong solution of hydrochloric acid. In contrast, saline treated rats suffered severe gastric erosion and hemmorrhage. In vitro transport studies have confirmed these findings, demonstrating that acid ($H^+$) diffuses much more slowly across gastric mucosa exposed to luminal phospholipid surfactants than across untreated tissue.

DESCRIPTION OF THE LIPID COMPOUNDS

As noted, the present invention is directed to charged and neutral lipids in general, and more particularly, to phospholipids, sterols and triglycerides which are formulated into unique anti-ulcer compositions useful to inhibit or retard ulcerogenesis. The phospholipids and triglycerides of the present invention generally fall into two categories depending on the nature of their aliphatic substitutions, i.e., whether saturated or unsaturated.

As used herein, a saturated phospholipid or triglyceride is one in which all of the aliphatic substitutions are saturated and thus do not contain c=c double bonds. Conversely, unsaturated phospholipids are triglycerides having at least one unsaturated aliphatic substitution defined as including one or more c=c double bonds.

The phospholipids of the present invention are characterized generally by the formula

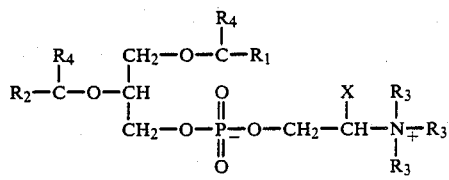

wherein $R_1$ and $R_2$ are saturated aliphatic substitutions ranging from 8 to 32 carbon atoms; $R_3$ is H or $CH_3$, and X is H or COOH; and $R_4$ is $=O$ or $H_2$.

As will be appreciated by those of skill in the art, the foregoing chemical structure defines a zwitterionic phospholipid structure and embraces a wide range of phospholipids, including but not limited to phosphatidyl cholines, phophatidyl ethanolamines, phosphatidyl serines and various other zwitterionic phospholipids. A further listing of saturated and unsaturated fatty acid groups that can be esterified or ether-linked to the phospholipid in question can be found in Table 1. However, as will be appreciated, these listings are not intended to be a complete listing of useful phospholipids, and its inclusion herein is for the reader's convenience and to disclose Applicant's preferred embodiments.

Phospholipid compounds found to be particularly useful in the practice of the present invention are dilinoleoyl-phosphatidylcholine (DLL-PC), dipalmitoyl-phosphatidylcholine (DPPC) and egg phosphatidycholine (Egg-PC or $PC_e$). In DPPC, a saturated phospholipid, the saturated aliphatic substitution $R_1$ and $R_2$ are $CH_3-(CH_2)_{14}$, $R_3$ is $CH_3$ and X is H. In DLL-PC, an unsaturated phospholipid, $R_1$ and $R_2$ are $CH_3-(CH_2)_4-CH=CH-CH_2-CH=CH-(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid).

The sterol compounds of the present invention are defined generally by the formula

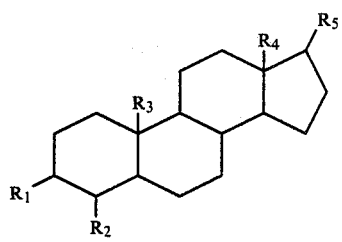

wherein the sterol contains zero, one or multiple double bonds in the perhydrocyclopentanophenanthrene ring; $R_1$ is either an H, O (ketone) or OH; $R_2$, $R_3$ and $R_4$ are either H or $CH_3$; and $R_5$ is a aliphatic chain of between 1 and 10 carbon atoms in length.

The most common sterol included by this structure, and the one preferred for the preparation of the various sterol-containing compositions disclosed herein, is cholesterol. Cholesterol is typically preferred due to its ready availability, low cost and relative lack of toxicity or biological/hormonal activity. However, other sterols of this general structure may be employed where desired including, for example, beta-sitosterol and desmosterol.

The triglycerides of the present invention are generally characterized by the formula

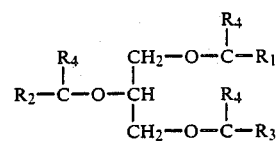

wherein $R_1$, $R_2$ and $R_3$ are each aliphatic substitutions ranging from 4 to 32 carbon atoms; and $R_4$ is either $=O$ or $H_2$.

As will be appreciated, this structure embraces a wide range of triglycerides, both saturated and unsaturated, and include, for example, triglycerides such as tripalmitin (saturated), triolein and trilinolein (both unsaturated). A further listing of saturated and unsaturated fatty acids that can be esterified or ether-linked to the triglyceride in question is displayed in Table I below. However, this table is included for convenience only and is merely representative of a variety of useful triglycerides and is therefore not intended to be inclusive.

TABLE I

FATTY ACIDS THAT MAY BE ESTERIFIED TO PHOSPHOLIPIDS AND TRIGLYCERIDES

A. Saturated Fatty Acids

| | |
|---|---|
| n-Butyric acid (butanoic acid) | Stearic acid (octadecanoic acid) |
| n-Valeric acid (pentanoic acid) | Nondecylic acid (nonadecanoic acid) |
| Caproic acid (hexoic acid, hexanoic acid) | Arachidic acid (eicosanoic acid) |
| Enanthic acid (heptanoic acid) | Heneicosanoic acid |
| Caprylic acid (octanoic acid) | Behenic acid (dososanoic acid) |
| Pelargonic acid (nonanoic acid) | Tricosanoic acid |
| Capric acid (decanoic acid) | Lignoceric acid (tetracosanoic acid) |
| Undecylic acid (hendecanoic acid) | Pentacosanoic acid |
| Lauric acid (dodecanoic acid) | Cerotic acid (hexacosanoic acid) |
| Tridecylic acid (tridecanoic acid) | Heptacosanoic acid |
| Myristic acid (tetradecanoic acid) | Montanic acid (octacosanoic acid) |
| Pentadecylic acid (pentadecanoic acid) | Nonacosanic acid |
| Palmitic acid (hexadecanoic acid) | Melissic acid (triacontanoic acid) |
| Margaric acid (heptadecanoic acid) | Lacceroic acid (dotriacontanoic acid) |

B. Unsaturated Fatty Acids

| | |
|---|---|
| trans-Crotonic acid (trans-butenoic acid) | $\Delta^{11}$-Eicosenoic acid |
| Iso-crotonic acid (cis-butenoic acid) | Cetoleic acid ($\Delta^{11}$-docosenoic acid) |
| $\Delta^3$-Hexenoic acid | Erucic acid (cis- $\Delta^{12}$-docosenoic acid) |
| $\Delta^4$-Decenoic acid (obtusilic acid) | Brassidic acid (trans- $\Delta^{13}$-docosenoic acid |
| $\Delta^9$-Decenoic acid | Selacholeic acid (nervonic acid, cis- $\Delta^{15}$-tetracosenoic acid) |
| $\Delta^4$-Dodecenoic acid (linderic acid) | Ximenic acid ($\Delta^{17}$-hexacosenoic acid) |
| $\Delta^5$-Dodecenoic acid | Sorbic Acid |

TABLE I-continued

FATTY ACIDS THAT MAY BE ESTERIFIED TO PHOSPHOLIPIDS AND TRIGLYCERIDES (lauroleic acid)
$\Delta^9$-Dodecenoic acid $\Delta^4$-Tetradecenoic acid
(tsuzuic acid)

$\Delta^5$-Tetradecenoic acid
(physeteric acid)

$\Delta^9$-Tetradecenoic acid
(myristoleic acid)

$\Delta^9$-Hexadecenoic acid
(palmitoleic acid)

cis-$\Delta^6$-Octadecenoic acid
(petroselinic acid)

Oleic acid
(cis-$\Delta^9$-octadecenoic acid)

Elaidic acid
(trans-$\Delta^9$-octadecenoic acid)

trans-Vaccenic acid
(trans-$\Delta^{11}$-octadecenoic acid)

cis-Vaccenic acid
(cis-$\Delta^{11}$-octadecenoic acid)

$\Delta^{12}$-Octadecenoic acid

Gadoleic acid
($\Delta^9$-eicosenoic acid)

$\Delta^{2,4}$-hexadienoic acid)
Linoleic acid
(cis-cis- $\Delta^{9,12}$-octa-
decadienoic acid)
Hiragonic acid
($\Delta^{6,10,14}$-hexa-
decatrienoic acid)
alpha-Eleostearic acid
(cis- $\Delta^{9,11,13}$-octa-
decatrienoic acid)
beta-Eleostearic acid
(trans- $\Delta^{9,11,13}$-octa-
decatrienoic acid)
Linolenic acid
($\Delta^{9,12,15}$-octa-
decatrienoic acid)
Stearidonic acid
(moroctic acid,
$\Delta^{4,8,12,15}$-octa-
decatretraenoic acid)
Timnodonic acid
($\Delta^{4,8,12,15,18}$-
eicosapentaenoic acid)
Arachidonic acid
($\Delta^{5,8,11,14}$-eicosa-
tetraenoic acid)
Clupanodonic acid
($\Delta^{4,8,12,15,19}$-doco-
sapentaenoic acid)
Nisinic acid
($\Delta^{4,5,12,15,19,21}$-
tetracosahexaenoic acid)
Thynnic acid
(hexacosahexa-
enoic acid)

FORMULATION AND ADMINISTRATION OF ANTIULCER COMPOSITIONS

As noted above, it has been found that not all phospholipid-containing compositions function with adequate efficacy to render them particular useful pharmacologically. Through extensive experimentation, Applicant has determined that while saturated phospholipids, for example, DPPC, exhibit a certain degree of antiulcer or ulcer preventative effect alone, the addition of a triglyceride (preferably saturated) to saturated phospholipid-containing compositions improves their activity to an amazing and unexpected degree.

Conversely, compositions which include only an unsaturated phospholipid, for example, Egg-PC or DLL-PC, show virtually no antiulcer activity alone. However, the addition of a sterol such as cholesterol surprisingly renders such compositions very active. Moreover, the further addition of a triglyceride, whether saturated or unsaturated, further enhances the activity of unsaturated phospholipid/sterol compositions.

It is also of interest to note that the activity of unsaturated phospholipid/sterol compositions is lost if the sterol employed contains an aliphatic ester at the 3-position in place of the OH group of ring A of the sterol moiety.

The method of formulation of the various antiulcer composition does not appear to be particularly crucial. As noted, protective effect can be obtained, for example, by simple direct administration of the lipids to a selected luminal surface. However, for most applications it will generally be desirable to provide the lipids in the form of a colloidal or liposomal suspension of the selected composition in an pharmaceutically acceptable aqueous diluent. While virtually any pharmaceutically acceptable aqueous diluent may be employed, it has generally been found that a certain level of salt, for example in the form of isotonic saline has significant anti-ulcer activity. Further, small amounts of heavy metals (or other polyvalent cations) or anti-oxidant chemicals with the capability of scavenging free radicals can be added to the diluent to provide a lipid composition of greater anti-ulcer efficacy, stability and lumen-coating effectiveness.

Colloidal suspensions are typically formulated to achieve concentration of about 0.5 to 20 grams total lipid for each final milliliter of aqueous suspension, or more preferably, between about 1 and about 5 mg/ml. Although the particular methodology is not critical, it is preferred to provide the selected weighed lipid components in a suitable container, followed by addition of the aqueous diluent in suitable proportions to achieve the desired final concentration of lipids. The entire admixture is then vortexed or sonicated for several minutes (at temperatures up to and above the transition temperature of the lipid, generally 4°–50° C. to achieve the final colloidal suspension.

The lipids may be stored prior to suspension formulation by dissolving known amounts in chloroform or the like. In this manner, aliquots containing known amounts of the selected lipid or lipid mixtures may be added to the mixing container, the chloroform evaporated off, and the aqueous diluent added.

It will be appreciated that in certain aspects the foregoing formulation procedure resembles procedures employed in the art for liposome preparation. Liposomes are multi- or unilamellar membranous structures which are commonly employed for encapsulation of lipophilic substances, such as various pharmaceutical agents. Liposomes are typically formed by sonication of aqueous dispersions of phospholipids in either the presence or absence of cholesterol in a manner which allows the lipid structures to associate into organized bilayer membraneous structures.

It is stressed, however, that there is no requirement that liposomes be made in order to achieve useful lipid compositions in accordance with the present invention. For example, disrupted or aggregated liposomes, or nonliposomal dispersions, appear to be at least as efficacious as intact liposomes. Moreover, except in the case of unsaturated phospholipid-containing compositions, sterols should be excluded from the formulation. Thus, although sonication of the admixture is preferred for mixtures containing saturated triglycerides, simple vortexing or otherwise similarly agitating the mixture will be sufficient. It also should be emphasized that in the presence of triglycerides the lipid suspension readily sediments. This suggests that the liposomes have fused to form either large dense multilamellar vesicles, lipid aggregates, stable fat globules or lipid sheets. All of the above physical forms have been observed in the suspensions under electron microscopic examination. These physical forms, thus, would have little or no luminal space as would a classical liposomal structure. However, all such preparations generally exhibit equally high activity independent of the lipid structure formed.

Regardless of the particular preparation method employed or type of suspension obtained, a sufficient amount is administered to adequately cover the desired tissue or luminal surface. Generally, sufficient coverage is obtained for oral application to the stomach by administering 0.5 ml to 20 milliliters of a 0.1 to 10 g.lipid/ml. suspension per application, depending on the particular lipid mixture and the severity of the disease being treated. However, as will be appreciated, dosages of the formulations are not known to be particularly limited by any toxicity problems.

In addition to being useful in treating or preventing gastric ulcer disease, it is contemplated that the present formulations will prove useful in the treatment of any number of ulcerative or degenerative processes of the luminal lining of the G.I. tract, particularly in those areas of the G.I. tract that rely on an intact hydrophobic barrier for normal function. As measured by the contact angle technique which measures the hydrophobic character of a surface (see, e.g., Hills et al. (1983) *Am. J. Physiol.*, 244:G561), it has been found that long stretches of the G.I. lumen, including for example the lower bowel, stomach and esophagus, are naturally quite hydrophobic. Such hydrophobic regions, and degenerative processes affecting such regions, are thus all candidates for beneficial therapy in accordance with the present invention. Moreover, specific ulcerative processes such as necrotizing enterocolitis and inflammatory bowel disease (e.g., ulcerative colitis and Crohn's disease) are believed to be amenable to hydrophobic treatment.

Other candidates include inflammatory processes such an inflammation of the esophagus (esophagitis). It has been found that many inflammatory processes are accompanied by decreases in the hydrophobic character of the affected tissue. In that it is postulated that this hydrophobic character serves to protect the underlying epithelium from injury, infection and inflammation, it is proposed that by maintaining the hydrophobic character of the tissue surface through the application of the present formulations, the protective barrier is reinforced.

Other related applications include application to the epidermal, vaginal or corneal epithelium as a method for treating inflammation or ulceration in these respective tissues. Moreover, due to the highly water impermeable and hydrophobic character of the urinary bladder, and the fact that a reduction in these properties can predispose the bladder to infection, it is proposed that the present formulations will prove beneficial in treating or preventing bladder infections.

EXAMPLES ILLUSTRATING PREFERRED EMBODIMENTS

The following examples are representative experiments which have been included herein to illustrate Applicant's preferred embodiments. Most of the experiments were conducted in an experimental system designed to compare the ulcer protective efficacy of various lipid preparations versus saline controls. In this system, unless otherwise indicated, rats were intragastrically treated with 1 ml of a lipid test solution, generally at a total lipid concentration of 3 mg/ml, 2 hours before intragastric challenge with 1 ml of 1.0N HCl or 100% ethanol. The rats were sacrificed 1 hour later at which time the lesion length resulting from the acid challenge was measured in a blind or double-blind fashion.

These experiments therefore provide a model for directly comparing the activity of the various ulcer-protective compositions, and further, provide a reasonable basis from which to determine their relative ulcer-protective efficacy and dosages in humans. In addition, a set of experiments is included to demonstrate the ability of the present compositions to maintain the hydrophobicity of the luminal lining upon ulcerogenic challenge. The correlation between the ulcer-protective and hydrophobicity-maintaining activities of the compositions therefore becomes readily apparent.

For the following experiments, the following protocols were utilized for the preparation of lipid suspensions. The selected phospholipids, triglycerides and/or sterols were weighed in a screw cap vial and then dissolved in about 5 ml. chloroform. The chloroform was then evaporated under a stream of $N_2$ gas at room temperature. An amount of a solution of 0.86% NaCl in distilled water (pH 7.0) was then added which was sufficient to provide the final selected concentration. For mixtures of saturated phospholipids with saturated triglycerides (e.g.-DPPC+TP) and unsaturated phospholipids+sterol+saturated triglycerides (e.g.-DLL-PC=CHOC+TP), the mixtures were then sonicated for 15 minutes at room temperature. For compositions of a unsaturated phospholipid+sterol+unsaturated triglyceride (e.g.- $PC_e$=CHOL+TO), the mixtures were vortexed for 2 minutes at room temperature. Additionally, for lipid mixtures which included a triglyceride, the mixture was capped under an $N_2$ environment prior to agitation.

The contact angle test was employed to compare and illustrate the ability of the three principal lipid composition embodiments to maintain the hydrophobic character of the luminal lining upon ulcerogenic challenge with one of three ulcerogenic agents, 1.0N HCL, 100% ethanol and 10% acetic acid (the latter administered to the colonic epithelium by enema). The tests were performed basically as described in Hills et al. (1983), *Am. J. Physiol.*, 244:G561, except using rat oxyntic tissue. The contact angle test relies on the finding that the contact angle subtended between a droplet of aqueous fluid and a nonwettable surface provides a direct estimation of the degree of hydrophobicity of the surface.

Hydrophobicity is characterized by any tendency of a fluid to form beads on the surface rather than to spread evenly. A quantitative index for this phenomenon is obtained by measuring the contact angle. This is the angle between the solid-liquid and liquid-air interfaces at the triple point where solid, liquid, and air meet. It can vary from 0° for a perfectly wetted surface up to values of the order of 108° for water on a particularly hydrophobic surface such as Teflon.

In the present experiment, a section of rodent oxyntic (or colonic) tissue (5×15 cm) was carefully excised, laid flat, and gently wiped free of gastric contents and mucus. The mucosal surface was then lightly rinsed with saline before being transferred to the flat horizontal stage of a goniometer, which is the standard instrument for measurement of any contact angle. Any excess rinse solution was removed by gentle blotting, and the tissue was stabilized at 25° C. for 5 min.

Contact angle is a basic surface parameter and one very commonly measured on human skin by cosmetic chemists. The standard equipment for its determination is a goniometer (Rame-Hart model 100-00 115) fitted with a monochromatic light source, camera attachment, and micrometer-activated syringe (Rame-Hart 100-10) for applying small volumes of saline to either the treated or control tissue surfaces. Five microliters of normal saline were applied to the luminal surface of the tissue and the contact angle was measured in the standard way.

The center of the field of view was adjusted to coincide with the triple point, and then one cross hair was adjusted to coincide with the tissue-fluid interface and the other to present a tangent to the liquid-air interface. The angle between the two is the contact angle and can be read off directly from the scale encircling the eyepiece. Magnification ($\times 25$) of the triple point enables the observer to allow for tissue irregularity in measuring contact angle. The effects of micro irregularities is a subject of discussion among physicists, but the macro value is still a good reflection of the micro value. Contact-angle determinations were repeated at two or more other sites on the sample, all within the oxyntic (or colonic) region of the mucosa.

For the results displayed in Table II, the three general embodiments of lipid compositions were employed to demonstrate their ability to protect the "contact angle" (i.e., hydrophobicity) of the rat oxyntic tissue upon ulcerogenic challenge. The three exemplary combinations comprised (1) a saturated phospholipid and saturated triglyceride (DPPC-TO); (2) an unsaturated phospholipid, a sterol and saturated triglyceride (DLL-PC-TP); and (3) an unsaturated phospholipid, sterol and unsaturated triglyceride ($PC_e$CH-TO).

As shown in Table II, the two gastric ulcerogens, ETOH and HCl, were found to reduce the observed contact angle 1 hr after intragastric administration from an average of about 36° (control-untreated) to about 8° and 5° (control-treated), respectively. However, pretreatment with any one of the three lipid composition groups almost entirely reversed the effect of the ulcerogens. The DPPC-TP treatment was found to provide the most effective barrier to hydrophobic erosion, with DLL—PC—TP and $PC_e$CH—TO providing a reduced but nevertheless effective barrier.

TABLE II

CONTACT ANGLE[a] MAINTENANCE BY MIXTURES OF POLAR AND NON-POLAR LIPIDS

| Challenge-Test Soln | PRETREATMENT | | | |
|---|---|---|---|---|
| | Saline | $PC_e$CH-TO | DLL-PC-TP | DPPC-TP |
| Saline | 36.2 ± 0.8 (control) | 38.0 ± 0.9 | 46.3 ± 4.2 | 39.9 ± 0.8 |
| 100% ETOH | 8.3* ± 2.2 | 25.5** ± 3.2 | NT | 37.0** ± 2.7 |
| 1.0 N HCL | 5.2* ± 2.8 | 27.9** ± 1.7 | 30.9** ± 2.7 | 36.0** ± 1.3 |

[a]Values are mean ± SEM of gastric contact angles (degrees) measured at sacrifice, 3 hrs after pretreatment and 1 hr after challenge.
Abbreviations: NT = Not tested; ETOH = ethanol; $PC_e$CH-TO = Mixture of egg Phosphatidylcholine + 50 M% cholesterol (1 mg/ml) + Triolein (4 mg/ml); DLL-PC-TP = Mixture of Dilinoleoyl Phosphatidylcholine + 80 M% cholesterol (1 mg/ml) + Tripalmitin (10 mg/ml); DPPC-TP = mixture of dipalmitoyl Phosphatidylcholine (1 mg/ml) + Tripalmitin (4 mg/ml).
* = $p < 0.05$ vs contact angle values of controls (saline pretreated, saline challenged).
** = $p < 0.05$ vs. contact angle of rats pretreated with saline and challenged with either 100% ETOH, or 1N HCL.

Referring now to FIG. 1 is shown the first of a series of experiments employing the reduction in lesion length test system as an indication of ulcer protective action. In the FIG. 1 experiment, the ulcer protective activity of various combinations of an unsaturated phospholipid, Egg Pc ($PC_e$), and a sterol (cholesterol) were compared to a saline control. In these experiments, 1 ml of the lipid solution was intragastrically administered to rats two hours before the animals were challenged with 1 ml of 1N HCl. The rats were sacrificed 1 hr later at which time lesion score was quantified.

As will be readily appreciated from FIG. 1, although neither $PC_e$ nor cholesterol were found to protect against acid-induced gastric lesions on their own, combination of the agents ranging between 60 and 20 mole % cholesterol (i.e., between 40 and 80 mole % $PC_e$) were found to provide a strong and unexpected protection to the stomach. A maximum of 85% reduction in lesion length was observed with a 50/50 mole % mixture of cholesterol and $PC_e$.

In FIG. 2, a similar experiment was performed with a composition containing dilinoleoyl phosphatidyl choline (DLL—PC) and cholesterol. In this experiment, it was found that a similar range of molar percentages provided roughly similar activity. However, in this case, a maximal reduction in lesion length of 85% was observed with a mixture of 20 mole % DLL—PC and 80 mole % cholesterol.

FIG. 3 illustrates the long-lasting ulcer protective action of the most preferred combinations from the FIG. 1 and 2 experiments. Here it was demonstrated that both combinations, $PC_e$+50% Chol. and DLL—PC+80% Chol., were both capable of maintaining protective activity if administered either 2 or 4 hrs prior to the acid challenge. Moreover, $PC_e$+50% Chol. was found to provide some protection even at 6 hours post-administration.

Figure 4:
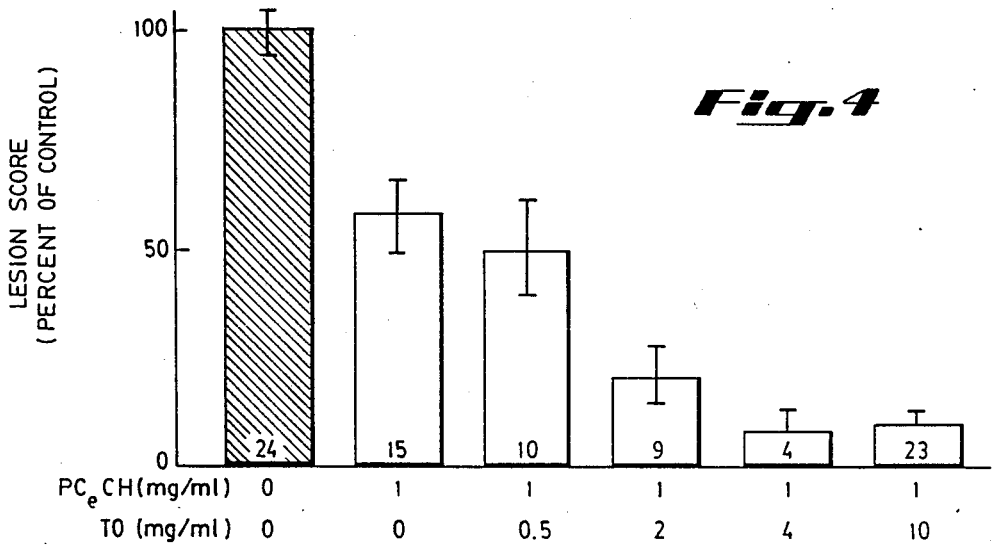
FIG. 4. This figure demonstrates that the protective action of a lower dose (1 mg/ml) of the $PC_e$+50M % Chol ($PC_e$ CH) mixture (to approximate the $ED_{50}$) could be significantly enhanced in a dose dependent fashion by the addition of the triglyceride, triolein (TO), to the mixture. Although not shown here, TO on its own (10 mg/ml) had only a small protective action (<20% reduction in lesion score) against acid-induced lesions.
Figure 5:
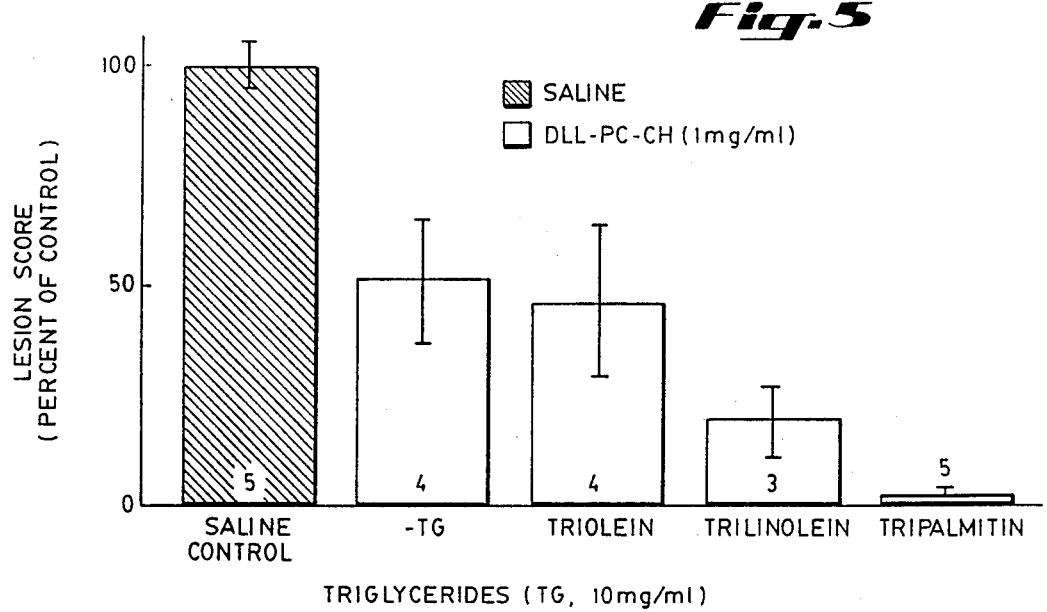
FIG. 5. Effect of different triglycerides(TG) on protective action of lipid mixtures of di-linoleoylphosphatidylcholine and 80M % cholesterol (DLL-PC-CH) against acid-induced gastric lesons. This figure graphically illustrates that the addition of Tripalmitin and Trilinolein to an $ED_{50}$ dose (1 mg/ml) of the DLL+80M % Chol mixture enhanced the protective efficacy of the suspension, whereas addition of TO to the mixture was only minimally effective.

In FIGS. 4 and 5, the ulcer-protective efficacy of unsaturated phospholipid/cholesterol combinations are shown to be surprisingly enhanced upon the inclusion of a triglyceride. In particular, in FIG. 4 it is shown that the inclusion of up to 10 mg/ml of an unsaturated triglyceride, triolein (TO), in a 1 mg/ml combination of $PC_e$ and 50 mole % cholesterol ($PC_e$CH) greatly improved its efficacy. A maximum reduction in lesion length of >90% was observed with the combination of 1 mg/ml $PC_e$CH and 4 mg/ml TO.

In FIG. 5, a similar experiment is shown for the combination of dilinoleoyl phosphatidylcholine and 80 mole % cholesterol (DLL—PC—CH) with each of three different triglycerides. Two of the triglycerides employed, triolein (TO) and Trilinolein (TL), were saturated triglycerides, while the third, tripalmitin (TP), was a saturated triglyceride. The DLL—PC—CH was employed at its $ED_{50}$ (1 mg/ml) with the various triglycerides being included at 10 mg/ml. As will be appreciated from the data displayed in FIG. 5, tripalmitin was found to be the most efficacious triglyceride additive, with an observed reduction in lesion length of about >95%. Triolein was found to be the least effective triglyceride additive, with trilinolein somewhere in between.

In the series of experiments represented by Table III below, the effect of esterification of cholesterol at carbon position 3 on the ulcer protective activity of DLL—PC was investigated. In general, the results indicated that cholesterol esters of this type were not capable of lending an gastric protective effect to DLL—PC.

TABLE III

Effect of Cholesterol and Cholesterol Esters[a]
on Gastric Protective Effect of Lipid
Suspensions of Dilinoleoyl-Phosphatidylcholine
(DLL-PC) Against Acid-Induced Lesions[b]

| Pretreatment Test Solution | n | Lesion Score (% of control) |
| --- | --- | --- |
| Saline | 10 | 100 ± 9.4 |
| DLL-PC + Cholesterol | 3 | 28.1 ± 1.7* |
| DLL-PC + Cholesteryl-arachidonate | 3 | 92.8 ± 13.2 |
| DLL-PC + Cholesteryl-n-butyrate | 5 | 109.0 ± 11.9 |
| DLL-PC + Cholesteryl-linoleate | 4 | 118.3 ± 20.8 |
| DLL-PC + Cholesteryl-oleate | 4 | 83.8 ± 13.4 |
| DLL-PC + Cholesteryl-palmitate | 5 | 74.8 ± 12.1 |

[a]Cholesterol or cholesterol esters added at a conc. on 80 M % (total lipid conc. = mg/ml).
[b]Gastric lesion induced by the intragastric administration of 1 ml of 1N HCl two hrs after they have been pretreated with 1 ml of either saline (controls) or the liposomal test solutions. Animals were sacrificed 1 hr after acid-challenge.
* = $p < 0.05$ vs lesion score of controls.

Figure 6:
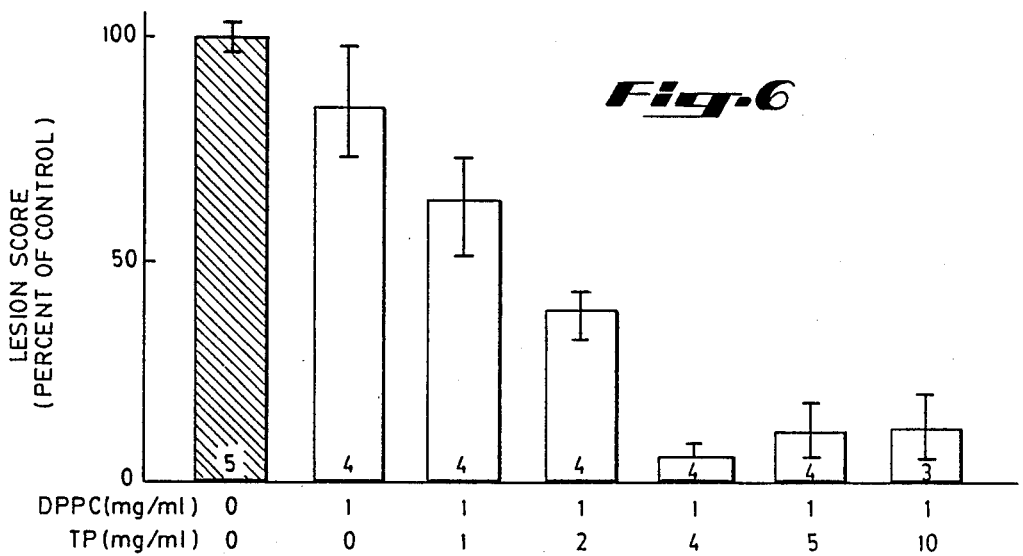
FIG. 6. Dose-dependance of tripalmitin(TP) on the protective effect of mixtures of dipalmitoyl-phosphatidylcholine(DPPC) against acid-induced gastric lesion. This figure demonstrates that the protective action of low doses of DPPC (1 mg/ml) could be enhanced in a dose-dependent fashion by the addition of Tripalmitin (TP) to the mixture. Although not shown here TP on its own (10 mg/ml) had only a modest protective action, reducing lesion score by 50-60%.

In FIG. 6, the gastric protective activity of compositions including a saturated phospholipid, DPPC, together with a saturated triglyceride, TP, is disclosed. As will be appreciated, some protective effect was observed with the saturated phospholipid alone in that DPPC alone at 1 mg/ml was capable of providing a reduction in lesion length of about 10%. However, the inclusion of varying concentrations of a saturated triglyceride greatly enhanced the activity of DPPC. The most profound effect was obtained with compositions of 1 mg/ml DPPC together with 4 mg/ml TP, at which concentration a greater than >95% reduction in lesion length over control was observed.

Figure 7:
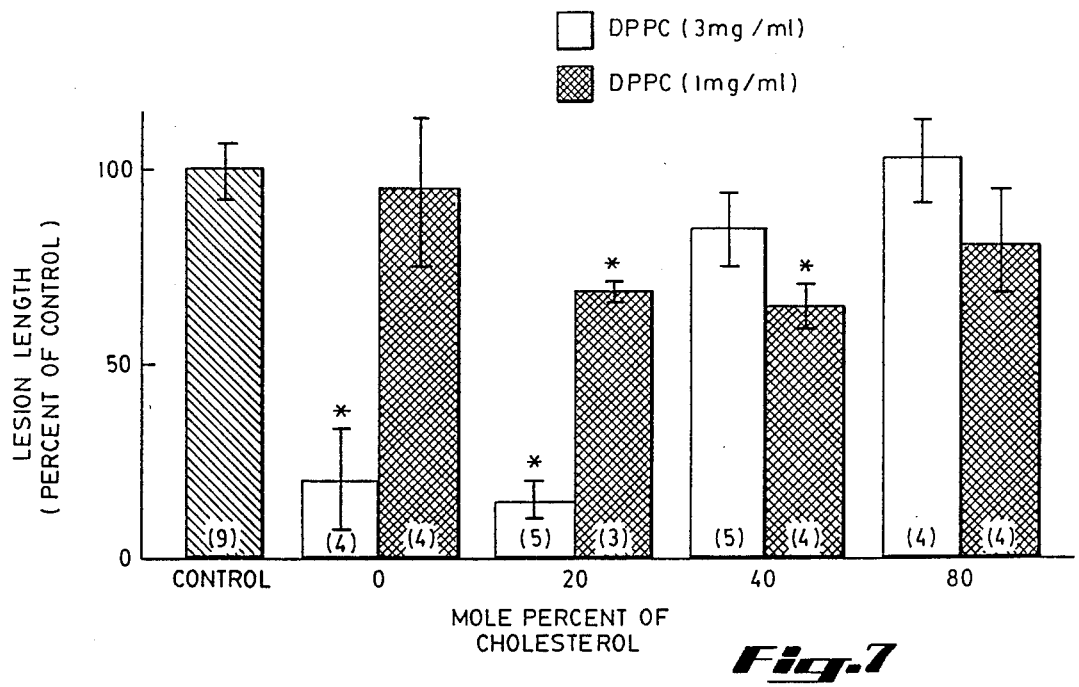
FIG. 7. The data presented here show that in contrast to the ability of Chol to augment the protective action of the unsaturated phospholipids, $PC_e$ and DLL-PC, addition of Chol to liposomes of the saturated phospholipid, DPPC, either had no effect (1 mg/ml) or in fact, inhibited the protective efficacy of higher concentrations of DPPC (3 mg/ml).

Although, in general, saturated phospholipids alone, as observed in FIG. 6, were capable of providing a protective effect, it was found that the addition of increasing amounts of cholesterol to saturated phospholipid preparations progressively reduced their observed activity. These data are displayed in FIG. 7. In particular, when cholesterol was added to a 3 mg/ml preparation of DPPC ($ED_{50}$ dose) at mole % ratios of greater than 20 mole %, the protective activity of DPPC was lost. This therefore demonstrates that cholesterol should not be included in lipid compositions based on saturated phospholipids.

Figure 8:
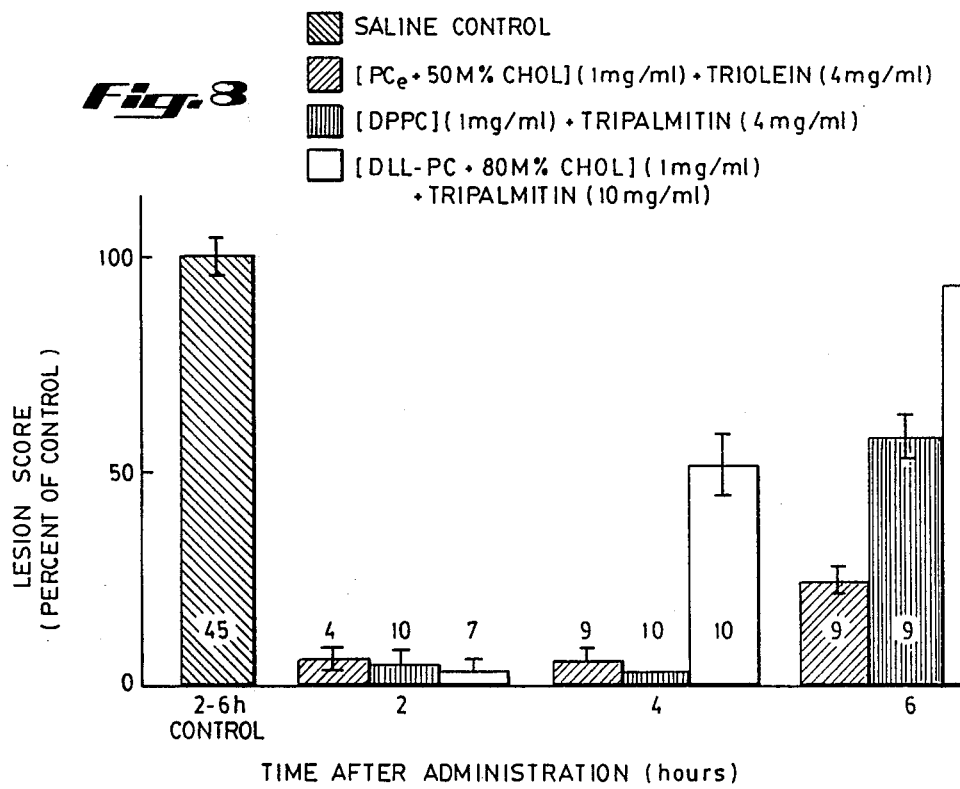
FIG. 8. Time-dependance of protective effect of mixtures of polar and non-polar lipids against acid-induced gastric lesions. This figure demonstrates that in addition to enhancing its efficacy, addition of the triglycerides (TG) to the mixtures of lipids appeared to prolong their duration of action [i.e. at 6 hrs—$PC_e$+50M % Chol+TO still reduced lesion score by 75%, whereas in the absence of the TG (See FIG. 3) it only reduced lesion score by 25%-6 hrs after administration].

FIGS. 8–10 represent experiments directed at comparing various aspects of the relative activity of the three general embodiments of the invention. In FIG. 8, the time-dependance of the protective effect of the three embodiments against acid-induced lesions is compared. As displayed therein, all three preferred embodiments gave very profound protective effect as of two hours post-administration. By 4 hours, the combination of unsaturated phospholipid+sterol+saturated triglyceride (DLL—PC+CHOL+TP) was found to be somewhat less active, but active nevertheless. The combinations of unsaturated phospholipid+sterol+unsatureated triglyceride ($PC_e$+CHOL+TO) and saturated phospholipid+saturated triglyceride (DPPC+TP) were found to retain virtually total activity at 4 hours. By six hours, the DLL—PC+-CHOL+TP treatment was almost devoid of activity, while the remaining combinations were still providing a significant degree of protection.

In FIG. 9, the direct protective effect of the same combinations against ethanol-induced gastric lesions were compared, with the combinations of unsaturated phospholipid+sterol+unsaturated triglyceride and saturated phospholipid+saturated triglyceride both exhibiting an almost equal high activity. While the unsaturated phospholipid+sterol+saturated triglyceride was found to be the least effective, it nevertheless exhibited significant activity.

In FIG. 10, the two most active combination were tested for the time-dependance of their protective effect against ethanol induced gastric lesions. As will be appreciated, both combinations exhibited excellent protective activity up through 6 hours post administration.

Tables IV and V depict a series of experiments conducted to demonstrate the surprising gastric protective efficacy of the lipid mixtures of the present invention when employed in combination with either polyvalent cations (Table IV) or antioxidants (Table V).

In Table IV it is shown that low (threshold) doses of the lipid mixtures alone achieved only mimimal reduction in lesion score. However, the addition of a polyvalent cation in the form of 0.2 mM $AU^{+++}$ ions resulted in a dramatic potentiation of the efficacy of lipid mixtures.

Similarly, Table V reflects data from experiments conducted employing the lipid mixtures in combination with various anti-oxidants. The results demonstrate that, as with polyvalent cations, the addition of anti-oxidant vitamins to the diluent potentiates the protective efficacy of the lipids.

This clear potentiative effect of the polyvalent cations and antioxidants with the lipid mixtures was indeed a surprising finding since at the concentrations employed neither gold salts nor vitamins A and C had any gastric protective activity on their own.

TABLE IV

Ability of Gold Salts[a] ($Au^{+++}$) to Enhance
the Protective Effect of Lipid Mixtures
Against Acid-Induced Gastric Ulcerogenesis

| Pretreatment | No. of Rats group | Lesion Score[d] (% of control) |
| --- | --- | --- |
| Phosphate Buffer (cotrol) | 5 | 100 ± 12 |
| $Au^{+++}$(0.2 mM)[a] | 5 | 83.6 ± 7.6 |
| $PC_e$ + Chol + TO[b] | 5 | 44.8 ± 5.8 |
| $PC_e$ + Chol + TO + $Au^{+++}$ [b,a] | 5 | 29.6 ± 10.0 |
| DPPC + TP[c] | 5 | 65.1 ± 11.5 |
| DPPC + TP + $Au^{+++}$ [c,a] | 5 | 9.7 ± 2.7 |

[a]Chloroauric Acid (0.2 mM) was made up in phosphate buffer (0.1 M, pH 7.0).
[b]$PC_e$ + 50 M % Chol (0.5 mg/ml) + 2 mg/ml TO
[c]DPPC (0.5 mg/ml) + 2 mg/ml TP
[d]Gastric lesions were measured 1 hr after acid challenge and 3 hrs prior to pretreatment.

TABLE V

Ability of Lipid-and-Water-Soluble Vitamins
with Anti-oxidant Activity to Enhance the
Gastric Protective Efficacy of Mixtures of Egg-
phosphatidylcholine ($PC_e$), Cholesterol and Triolein
($PC_e$ + Chol + TO) Against Acid-Induced Leions

| Pretreatment | No. of Rats group | Lesion Score[d] (% of control) |
| --- | --- | --- |
| Saline (control) | 4 | 100 ± 6.4 |
| $PC_e$ + Chol + TO[a] | 4 | 58.6 ± 6.9 |
| $PC_e$ + Chol + TO + Vit C[b] | 4 | 17.7 ± 3.3 |
| $PC_e$ + Chol + TO + Vit A[c] | 4 | 61.1 ± 10.5 |
| $PC_e$ + Chol + TO + Vit A, | | |

TABLE V-continued

Ability of Lipid-and-Water-Soluble Vitamins with Anti-oxidant Activity to Enhance the Gastric Protective Efficacy of Mixtures of Egg-phosphatidylcholine ($PC_e$), Cholesterol and Triolein ($PC_e$ + Chol + TO) Against Acid-Induced Leions

| Pretreatment | No. of Rats group | Lesion Score[d] (% of control) |
|---|---|---|
| + Vit C[b,c] | 4 | 12.8 ± 9.6 |

[a] $PC_e$ + 50 M % Chol (0.3 mg/ml) + 1.2 mg/ml TO.
[b] Vitamin C added at a final conc. of 20 mg/ml
[c] Vitamin A added to lipid in chloroform at a final conc of 1 mg/ml
[d] Gastric lesions were measured 1 hr after acid-challenge and 3 hrs prior to pretreatment To demonstrate the applicability of the present lipid compositions in the treatment of other gastrointestinal lesions, they were tested in an animal model designed to mimic the pathological changes associated with inflammatory bowel disease. In these experiments, the hydrophobicity of the colonic mucosa of rats was measured 5 days after the animals were administered enemas (0.5 ml) containing either saline (control) or 10% acetic acid (30 second rinse). It has been demonstrated in the scientific literature that administration of acetic acid by this route results in erosive and inflammatory changes in the colonic mucosa which resembles the pathological changes associated with inflammatory bowel disease.

In experimental rats, 0.5 ml of each of the three lipid mixtures (DPPC—TP, DLL—PC—Chol—TP, PCe—Chol—TO) was administered 2 hrs prior to and immediately following the acetic acid rinse. The results shown in Table VI below indicate that the rodent colonic mucosa is quite hydrophobic under control conditions and this non-wettable property is significantly reduced in response to experimentally-induced colitis. However, this transition from a non-wettable to a wettable state was reversed when the rats were treated with the unique mixtures of polar and non-polar lipids.

TABLE VI

Suface Hydrophobicity of the Rodent Colonic Mucosa in Experimentally-Induced Colitis: Ability of Lipid Mixtures to Maintain This Protective Hydrophobic Property

| Group Pretreatment | Acetic Acid | No. of rats group | Contact Angles |
|---|---|---|---|
| Saline | — | 3 | 60.7 ± 14.8° |
| Saline | + | 3 | 38.0 ± 3.2° |
| DPPC-TP | + | 4 | 79.8 ± 2.2° |
| PCe + Chol+ TO | + | 3 | 67.7 ± 7.1° |
| DLL-PC-Chol + TP | + | 4 | 59.3 ± 12.0° |

Further modifications and alternative embodiments of the compositions and methods of the present invention will be apparent to those skilled in the art in view of the foregoing description. Accordingly, this description is to be construed as illustrative only and is for the purpose of teaching those of skill in the art the manner of carrying out. It is understood that the embodiments of the invention herewith shown are to be taken as presently preferred embodiments. For example, equivalent elements or materials may be substituted for those illustrated and described herein. It is intended, therefore, that the following claims be interpreted to embrace all such modifications and changes.

What is claimed is:

1. A pharmaceutical composition comprising an ulcer protective amount of:

(a) a saturated phospholipid having the chemical structure

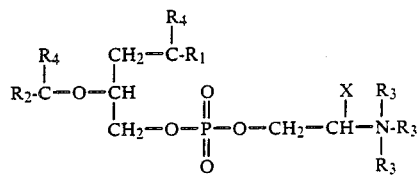

wherein $R_1$, $R_2$ and $R_3$ are either saturated or non-saturated aliphatic substitutions ranging from 4 to 32 carbon atoms; and $R_4$ is $=0$ or $H_2$; and (b) a triglyceride having the chemical structure

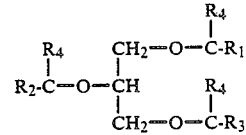

wherein R1, R2 and R3 are either saturated or non-saturated or non-saturated aliphatic substitutions ranging from 4 to 32 carbon atoms; and R4 is $=0$ or H2; wherein the saturated phospholipid and triglycerides are together in a pharmaceutically acceptable diluent, and the triglyceride concentration therein is about equal to or greater than the phospholipid concentration.

2. The composition of claim 1, wherein the saturated phospholipid comprises at least one esterified or ether-linked, saturated fatty acid selected from the group of saturated fatty acids consisting of: n-Butyric acid (butanoic acid); Stearic acid (octadecanoic acid); N-Valeric acid (pentanoic acid); Nondecylic acid (nonadecanoic acid); Caproic acid (hexoic acid, hexanoic acid); Arachidic acid (eicosanoic acid); Enanthic acid (heptanoic acid); Heneicosanoic acid; Caprylic acid (octanoic acid); Behenic acid (dososanoic acid); Pelargonic acid (nonanoic acid); Tricosanoic acid; Capric acid (decanoic acid); Lignoceric acid (tetracosanoic acid); Undecylic acid (hendecanoic acid); Pentacosanoic acid; Lauric acid (dodecanoic acid); Cerotic acid (hexacosanoic acid); Tridecylic acid (tridecanoic acid); Heptacosanoic acid; Myristic acid (tetradecanoic acid); Montanic acid (octacosanoic acid); Pentadecylic acid (pentadecanoic acid); Nonacosanic acid; Palmitic acid (hexadecanoic acid); Melissic acid (triacontanoic acid); Margaric acid (peptadecanoic acid); and Lacceroic acid (dotriacontanoic acid).

3. The composition of claim 1, wherein the triglyceride comprises at least one esterified or ether-linked fatty acid selected from the group of fatty acids consisting of: n-Butyric acid (butanoic acid); Stearic acid (octadecanoic acid); n-Valeric acid (pentanoic acid); Nondecylic acid (nonadecanoic acid); Caproic acid (hexoic acid, hexanoic acid); Arachidic acid (eicosanoic acid); Enanthic acid (heptanoic acid); Heneicosanoic acid; Caprylic acid (octanoic acid); Behenic acid (dososanoic acid); Pelargonic acid (nonanoic acid); Tricosanoic acid; Capric acid (decanoic acid); Lignoceric acid (tetracosanoic acid); Undecylic acid (hendecanoic acid); Pentacosanoic acid; Lauric acid (dodecanoic acid); Cerotic acid (hexacosanoic acid); Tridecylic acid (tridecanoic acid); Heptacosanoic acid; Myristic acid (tetradecanoic acid); Montanic acid (octacosanoic acid); Pentadecylic acid (pentadecanoic acid); Nonacosanic acid; Palmitic acid (hexadecanoic acid); Melissic acid (triacontanoic acid); Margaric acid (heptadecanoic acid); Lacceroic acid (dotriacontanoic acid); trans-Crotonic acid (trans-butenoic acid);$\Delta^{11}$-Eicosenoic acid; Iso-crotonic acid (cis-butenoic acid); Cetoleic acid ($\Delta^{11}$-docosenoic acid); $\Delta^3$-Hexenoic acid; Erucic acid (cis-$\Delta^{12}$-docosenoic acid); $\Delta^4$-Decenoic acid (obtusilic acid); Brassidic acid (trans-$\Delta^{13}$-docosenoic acid; $\Delta^9$-Decenoic acid; Selacholeic acid (nervonic acid, cis-$\Delta^{15}$-tetracosenoic acid); $\Delta^4$-Dodecenoic acid (linderic acid); Ximenic acid ($\Delta^{17}$-hexacosenoic acid); $\Delta^5$-Dodecenoic acid (lauroleic acid); Sorbic Acid ($\Delta^{2,4}$-hexadienoic acid); $\Delta^9$-Dodecenoic acid; Linoleic acid (cis-cis-$\Delta^{9,12}$-octadecadienoic acid); $\Delta^4$-Tetradecenoic acid (tsuzuic acid); Hiragonic acid ($\Delta^{6,10,14}$-hexa-ecatrienoic acid); $\Delta^5$-Tetradecenoic acid (physetericacid); alpha-Eleostearic acid (cis-$\Delta^{9,11,13}$-octa-decatrienoic acid); $\Delta^9$-Tetradecenoic acid (myristoleic acid); beta-Eleostearic acid (trans-$\Delta^{9,11,13}$-octa-decatrienoic acid); $\Delta^9$-Hexadecenoic acid (palmitoleic acid); Linolenic acid ($\Delta^{9,12,15}$-octa-decatrienoic acid); cis-$\Delta^6$-Octadecenoic acid (petroselinic acid); Stearidonic acid (moroctic acid,$\Delta^{4,8,12,15}$-octadecatretraenoic acid); Oleic acid (cis-$\Delta^9$-octadecenoic acid); Timnodonic acid ($\Delta^{4,8,12,15,18}$-eicosapentaenoic acid); Elaidic acid (trans-$\Delta^9$-octadecenoic acid); Arachidonic acid ($\Delta^{5,8,11,14}$-eicosa-tetraenoic acid); trans-Vaccenic acid (trans-$\Delta^{11}$-octadecenoic acid); Clupanodonic acid ($\Delta^{4,8,12,15,19}$-doco-sapentaenoic acid); cis-Vaccenic acid; Nisinic acid (cis-$\Delta^{11}$-octadecenoic acid); ($\Delta^{4,5,12,15,19,21}$-etracosahexaenoic acid); $\Delta^{12}$-Octadecenoic acid; Thynnic acid (hexacosahexa-enoic acid); Gadoleic acid ($\Delta^9$-eicosenoic acid).

4. The composition of claim 1 wherein the saturated phospholipid is dipalmitoyl phosphatidylcholine and the triglyceride is tripalmitin.

5. The composition of claim 1 or 4 wherein the phospholipid and the triglyceride are included in weight ratios of phospholipid to triglyceride ranging from 1:1 to 1:10.

6. The composition of claim 1 or 4 wherein the phospholipid and the triglyceride are included in weight ratios of phospholipid to triglyceride ranging from 1:2 to 1:5.

7. The composition of claim 1 further comprising a pharmaceutically acceptable amount of polyvalent ion.

8. The composition of claim 7 wherein the polyvalent ion is a polyvalent metal ion.

9. The composition of claim 8, wherein the polyvalent metal ion is copper, zinc, gold or aluminum ion.

10. The composition of claim 1 further comprising an effective amount of an antioxidant.

11. The composition of claim 10 wherein the antioxidant is vitamin A, E or C.

12. The composition of claim 1 further comprising an effective amount of an ulcerogenic non-steroidal anti-inflammatory or antipyretic agent.

13. The composition of claims 1 or 4 wherein the saturated phospholipid and the triglyceride are included in weight ratios of phospholipid to triglyceride of about 1:4.

14. A method of protecting the luminal lining of the gastrointestinal tract against ulceration, the method comprising administering an effective amount of a composition as defined by any one of claims 1 through 6 or 7 through 12, to the lining.

15. A method of reducing the ulcerogenic action of a non-steroidal antipyretic or anti-inflammatory agent on a patient comprising administering such an agent to the patient together with a composition as defined by any one of claims 1 through 6 or 7 through 12.

* * * * *

UNITED STATES PATENT AND TRADEMARK OFFICE
CERTIFICATE OF CORRECTION

PATENT NO. : 4,918,063
DATED : April 17, 1990
INVENTOR(S) : Lenard M. Lichtenberger It is certified that error appears in the above-identified patent and that said Letters Patent is hereby corrected as shown below:

In claim 1(a), line 5, column 22, insert -- O -- between "$CH_2$" and "C - $R_1$".

In claim 2, line 36, column 22, change the letter "N" to --n--.

In claim 2, line 51, column 22, delete the term "peptadecanoic" and insert the term --heptadecanoic--.

In claim 3, line 16, column 23, delete the term "ecatrienoic" and insert the term --decatrienoic--.

Signed and Sealed this

Twentieth Day of August, 1991

*Attest:*

HARRY F. MANBECK, JR.

*Attesting Officer*     *Commissioner of Patents and Trademarks*